United States Patent [19]

Cochrum et al.

[11] Patent Number: 5,015,476
[45] Date of Patent: May 14, 1991

[54] IMMUNIZATION IMPLANT AND METHOD

[75] Inventors: Kent C. Cochrum, Corte Madera; Lynnor B. Stevenson, Los Altos Hills; Scott R. King, San Francisco, all of Calif.

[73] Assignee: Paravax, Inc., Palo Alto, Calif.

[21] Appl. No.: 392,795

[22] Filed: Aug. 11, 1989

[51] Int. Cl.[5] .................. A61K 39/002; A61K 39/02; A61K 39/12; A61F 2/00
[52] U.S. Cl. .................................... 424/423; 424/88; 424/89; 424/92; 424/93; 424/422
[58] Field of Search .................. 424/422, 423, 88, 89, 424/92, 93

[56] References Cited

U.S. PATENT DOCUMENTS

| | | | |
|---|---|---|---|
| 4,673,566 | 6/1987 | Goosen et al. | 424/93 |
| 4,795,633 | 1/1989 | Murrell et al. | 424/88 |
| 4,798,786 | 1/1989 | Tice et al. | 424/93 |
| 4,803,168 | 2/1989 | Jarvis, Jr. | 424/422 |
| 4,808,404 | 2/1989 | Bhogal | 424/88 |

*Primary Examiner*—Thurman Page
*Assistant Examiner*—James M. Spear
*Attorney, Agent, or Firm*—William B. Walker

[57] ABSTRACT

Antigenic parasites are encapsulated in semipermeable polymeric envelope membranes to prepare implant capsules for immunizing an animal against parasitic infection. An animal may be immunized against parasitic infection by implanting into the animal the implant capsule at a location in the animal sufficient to stimulate a protective immune response in the animal to the parasite antigen.

32 Claims, No Drawings

IMMUNIZATION IMPLANT AND METHOD

BACKGROUND OF THE INVENTION

1. Field of the Invention

The present invention is directed to a method of immunizing mammals against parasitic infections. More specifically, the invention is directed to a method of immunizing mammals using an implanted capsule containing antigenic unicellular parasites, parasite larvae or cysts.

2. Discussion of the Background

Mammalian parasites present a health hazard to both animals and humans throughout the world. In the United States, parasitic infections of livestock present potential health hazards in the food supply. Improper handling, storage, processing and distribution operations in the food industry can result in opportunities for contamination with both spore and vegetative forms of parasites, ultimately presenting a health hazard to the human consumer. Control of parasitic infections in livestock is essential to maintaining a safe and healthy food supply and optimizing food resources.

Parasitic infections of domesticated animals result in substantial veterinary expense worldwide and in potential health hazards to the animal owner. For example, cats infected with toxoplasmosis present a serious health hazard to a developing fetus. Infection of the mother during pregnancy may result in severe central nervous system damage to the fetus.

In many parts of the world, protozoan parasitic diseases such as giardiasis, leishmaniasis, trypanosomiasis, malaria and amebic dysentery are endemic. These diseases present a constant health hazard to human travelers. Additional hazards are posed by common helminthic parasites.

Parasitic disease is also a large problem in military operations. Many parasitic worms and protozoa are endemic in tropical and subtropical parts of the world. Military personnel and animals that have lived in temperate climates are susceptible to attack by the infectious forms of parasites. In many parts of the world traditional control measures, especially control of vector populations with insecticides, are losing efficacy. Parasitic infections can cause severe morbidity and even death.

Over two billion people worldwide are infected with some kind of parasite. Hundreds of millions of humans have seriously impaired health due to parasitic infections. An estimated 200 million cases of schistosomiasis, 150 million cases of malaria, and 90 million cases of filarial worm infections are found in the tropical world. Parasites cause up to $1 billion loss in economic animals and about one half of the common problems in companion animals. Travel and migration are accelerating the spread of parasites and parasitic disease. These health hazards can be substantially reduced and possibly eliminated by the development of a safe and effective method of immunization against parasitic organisms.

The technology for immunizing against parasitic diseases is largely unknown. Attempts have been made to study the response of an animal to parasite implants, however. These studies involve isolation of the parasites from the host mammals immune system to determine the effect on the implant.

U.S. Pat. No. 3,629,390 describes an early attempt to provide controlled release of a bio-affecting preparation for avian applications in which a bioaffecting compound is formulated into particles of a solid matrix material which are gradually released subject to the grinding and abrading action occurring in the avian gizzard. Early attempts to enhance biocompatibility of biological materials in a mammalian host are described in U.S. Pat. No. 3,682,776 which teaches the treatment of transplant tissues with a protease inhibitor to prevent host rejection of the transplant and by U.S. Pat. No. 4,120,649 which teaches the treatment of transplant tissues with glutaraldehyde, a bifunctional cross-linking reagent, to provide a new contact surface in the transplant which is more favorably accepted by the host. These latter methods are not actual immunoisolation of the transplanted tissue, but rather surface modification to prevent tissue rejection.

Immunoisolation has been achieved with the use of implantable diffusion chambers which employ a microporous physical barrier separating the foreign cells or tissue from host immunological cells. Diffusion chambers are generally constructed from plastic rings or cylinders to which semipermeable membranes have been firmly attached. Diffusion chambers are relatively large having cross-sections ranging from approximately 10-20 mm. Materials for constructing diffusion chambers are commercially available.

Implantable diffusion chambers utilize semipermeable membranes which allow the selective diffusion of molecules in and out of the diffusion chamber but prevent the movement of cells, into the diffusion chamber. Much research has been focused on the use of diffusion chambers for treatment of diabetes. Using such methods, pancreatic islet cells are enclosed in a diffusion chamber which is then implanted in a diabetic mammal. Insulin diffuses through the semiporous diffusion chamber membrane and can ameliorate diabetic conditions for limited periods of time. See, for example, G.F. Klomp et al, Trans. Am. Soc. Artif. Intern. Organs, (1979), 25:74-76. Diffusion chambers in the form of artificial capillary units for use in treating diabetes have been described (A.M. Sun et al, Diabetes, (1977), 12:1136-1139). Diffusion chambers have also been used to study bacterial pathogenesis, e.g., Bordetella pertussis pathogenesis (K.D. Coleman and L.H. Wetterlow, Journal of Infectious Diseases, (1986), 154:33-39).

Diffusion chambers have been used to immunoisolate parasitic tissue or infective larvae in studies relating to the immune response of a host to parasitic infection. For example, diffusion chambers have been used to study response to Schistosoma mansoni (A.I. Kassis et al, Journal of Immunology, (1979), 123:1659-1662); Dipetalonema viteae (M. Tanner et al, Transactions of the Royal Society of Tropical Medicine and Hygiene, (1981), 75:173-174) and D. Abraham et al, Immunology, (1986), 57:165-169); Brugia pahangi (R. Chandrashekar et al, Parasite Immunology, (1985), 7:633-641 and J.P. Court, Tropenmed. Parasit., (1982), 33:83-86); Onchocerca volvulus (G. Strote, Trop. Med. Parasit., (1985), 36:120-122); Trypanosoma Cruzi (A. Sher et al, J. Protozool., (1983), 30:278-283); Ascaris suum (C.A. Crandall and V.M. Arean, Journal of Parasitology, (1964), 50:685-688); and Dirofilaria immitis (D. Abraham et al, J. Parasit., (1988), 74:275-282 and C.J. Delves, R.E. Howells, Trop. Med. Parasit., (1985), 36:29-31). None of these studies have attempted to immunize an animal against parasitic infection.

The use of diffusion chambers for encapsulation of tissues, cells or parasitic larvae is limited by the tendency of these relatively large chambers to become covered by a thick fibrous layer. Implantation of diffusion chambers, therefore, results in isolation of the diffusion chamber by the host immune system and provides limited utility in establishing immunity against parasitic infections. The use of diffusion chambers to provide immunity against parasitic infections is therefore unsuitable.

An alternative to the use of diffusion chambers is the microencapsulation of antigenic material in a semipermeable membrane. Microencapsulation differs from the use of diffusion chambers in several aspects. In microencapsulation processes, biological tissue or cells are encapsulated in a semipermeable membrane resulting in a product which is substantially smaller than a diffusion chamber. Microencapsulated tissue is not, in general, bioisolated by the host immune system in the same manner as diffusion chambers. As with diffusion chambers, substantial research in the field of microencapsulation has been directed to the treatment of diabetes and involves the encapsulation of pancreatic islet tissue (G.F. Klomp et al, loc. cit.; Tze et al, Transplantation Proceedings, (1982), 14:714–723; Leung et al, Artificial Organs, (1983), 7:208–212; Sun et al, Diabetes, (1977), 26:1136–1139; Lim et al, Science, (1980), 210:908–910; and U.S. Pat. No. 4,806,355). Microencapsulation of other mammalian tissues and cells are described, for example, in Lamberti et al, Abstract paper Amer. Chem. Soc., (1983), 85:162; Lamberti et al, Artificial Organs, (1984), 8:112; Lim and Moss, Journal of Pharm. Sciences, (1981), 70:351–354; Canadian patent 1,215,922 and U.S. Pat. No. 4,353,888.

The technology of microencapsulation as applied to transplant tissues and cells has been well described and elucidated. See for example U.S. Pat. Nos. 4,696,286; 4,407,957; 4,409,331; 4,391,909; 4,352,883 and 4,251,387. Microencapsulation techniques have been utilized to encapsulate drugs, mammalian tissues, isolated cells and bacterial cells.

The use of liposomes, i.e., vessels made of phospholipids, has been proposed for both drug delivery and the delivery of vaccines. Alving et al describe the effectiveness of liposomes as potential carriers of vaccines (C. Alving, et al, Vaccine, (1986), 4:166). The liposomes could carry cholera toxin, reducing toxicity while enhancing antigenicity. Human malaria sporozoite antigen, itself non-immunogenic, was found to induce antibodies when carried by liposomes.

The disadvantage of liposomes is that the particles are prone to being phagocytosed by cells of the reticular endothelial system, thereby destroying the source of antigenic material and preventing release of antigens. Further research is necessary to reduce the effect of phagocytosis sufficiently to allow the use of liposomes as slow release agents.

Implantation of diffusion chambers results in the partial biological isolation of the diffusion chambers by the immune system of the host mammal. Liposomes are rapidly phagocytosed by host immune cells. Accordingly, improved immunological methods and implants are desired to provide the required immunoisolation and establish the immunity necessary to protect against parasitic diseases in animals.

SUMMARY OF THE INVENTION

Accordingly, one object of the present invention is to provide a method of immunizing an animal by the implantation of an immunizing microcapsule into the animal such that immunity is established, wherein the implant provides immunoisolation from the host animal immune system.

A further object is an implant which provides for long-term slow release of parasite antigens and is constructed of biocompatible materials.

These and other objects which will become apparent from the following specification have been achieved by the present implant capsule for immunizing an animal against parasitic infection which comprises at least one antigen-producing parasite encapsulated within one or more semipermeable polymeric envelope membranes. The polymeric envelope membranes are permeable to antigenic components of the parasite and allow these antigens to diffuse from the implant capsule into the tissues of the host animal. The capsule envelope membranes are not permeable, however, to antibodies produced by the host animal. The parasite encapsulated within the polymeric envelope membranes may be any antigen-producing parasite capable of infecting an animal.

The invention is also directed to a method for immunizing an animal against parasitic infection. The present method involves implanting into an animal, an implant capsule comprising at least one antigen-producing parasite encapsulated within one or more semipermeable polymeric envelope membranes. The implant capsule is implanted at a location in the animal sufficient to stimulate a protective immune response to the parasite antigen.

DETAILED DESCRIPTION OF THE PREFERRED EMBODIMENTS

Prior methods of immunoisolating parasitic antigenic materials, including the use of diffusion chambers, adequately immunoisolate the antigenic material but stimulate only limited immunity due to the bioisolation of the diffusion chamber by the host animal's immune system. Antigen-producing parasites may be encapsulated in biologically compatible semipermeable polymeric membranes to form implant capsules which are not bioisolated by the host animal's immune system and are capable of the slow release of parasite antigens, thereby mediating long term immunity against parasite infection.

The present method involves isolation of appropriate antigen-producing parasites coating the parasites with an intermediate bonding layer, and microencapsulation of the coated parasites to form an implant capsule. The implant capsules of the present invention contain at least one parasite but may contain more than one organism depending on the process of encapsulation. Surprisingly, parasites remain viable for extended periods of time within the implant capsules and provide long term slow release of parasite antigens.

As used herein, "antigen-producing parasite" is used to mean any living form of a mammalian parasite which can excrete, secrete or otherwise produce diffusible parasite antigens after encapsulation in a semipermeable membrane.

The term "animal" as used herein refers to mammals and includes humans, livestock animals and domesticated pets, specifically. However, the method has application to all mammals which may be implanted and are capable of establishing a protective immune response to the implant capsule.

As used herein, the term "intermediate bonding layer" means a non-cytotoxic material capable of reducing the mobility of the parasite to be encapsulated. The intermediate bonding layer must also facilitate the subsequent encapsulation of the parasite by one or more polymeric envelope membranes.

By "semipermeable polymeric envelope membranes" it is meant any polymeric membrane which allows the diffusion of low molecular weight parasite antigens out of the present implant capsule but prevents the diffusion of high molecular weight proteins, such as antibodies, into the implant capsule. The polymeric envelope membranes of the present invention include membranes prepared from polyamino acid polymers, as well as biodegradable and/or biocompatible semipermeable membranes prepared by condensation reactions, anionic or cationic polymerization methods or by radical polymerization of a,B -unsaturated monomers, so long as the polymer has acidic (negatively charged) or basic (positively charged) side chain units.

The intermediate bonding layer used in the present invention must be non-cytotoxic to the parasite, contain one or more positively charged materials and, optionally function to reduce the mobility of the live parasite so that encapsulation is facilitated. The surface of biological membranes, including parasites, have a generalized negative charge. The intermediate layer, therefore, contains a material bearing a positive charge which can interact with the surface of the parasite and bond by electrostatic attraction. The intermediate bonding material may comprise a positively charged polymer or may comprise a mixture of a polymer capable of gelling and a second material bearing a positive charge. Further, the intermediate bonding material must be stable during the coating process and subsequent encapsulation processes and allow the diffusion of parasite antigens away from the parasite. The intermediate bonding material may be synthetic or natural, inorganic or organic so long as the properties identified above are present.

Specific materials which are suitable for the intermediate bonding material include polysaccharides, polysaccharide derivatives and polysaccharide-containing materials such as agar, agarose, algin, alginate, and mixtures thereof which are capable of gelling in combination with a second charged compound such as biocompatible metal salts or other positively charged polymers. Any material having appropriate gelling qualities which is non-cytotoxic and allows diffusion of parasite antigens away from the parasite, may be used as the intermediate bonding material.

A particularly preferred embodiment of the intermediate bonding material is the use of a polysaccharide such a agar or agarose in combination with a transition metal hydroxide capable of forming a gel, such as for example aluminum hydroxide. If desired, other polysaccharides such as alginate or chitosan may be used in place of agar or agarose or mixtures of alginate and/or chitosan with agar or agarose may be used in combination with aluminum hydroxide. In general, any combination of agar, agarose, alginate and chitosan in combination with aluminum hydroxide will provide a satisfactory intermediate bonding material.

In addition, adjuvants which stimulate production of antigens from the parasite, reduce mobility of the parasite, and which increase antigenicity in general in the host animal, may also be combined with the intermediate bonding material. Such adjuvants include antigenic polymers, lymphokines and/or cytokines such as chemotactins, interferons, interleukins, migration inhibition factors, macrophage activation factors, etc. The production and isolation of lymphokines and cytokines from lymphocytes is known. (See for example N.R. Rose, F. Milgrom and C.J. vanOss, Principals of Immunology, MacMillan Publishing Company, Inc., New York, 1973). The use of such adjuvants is particularly effective where the adjuvant can diffuse out of the implant capsule or is partially exposed to the host immune system. Preferred antigenic polymers include polytyrosine, polyhydroxybutyric acid, polylysine and polyornithine.

The polymeric envelope which surrounds the parasite and intermediate bonding layer may comprise one or a multiplicity of polymer layers. The first envelope membrane applied over the intermediate bonding layer should have a charge which is opposite to the overall charge on the intermediate bonding layer. That is, since the intermediate bonding layer has an overall positive charge, then a polymer membrane bearing negative charges should first be applied over the intermediate bonding layer. The opposite charges of the intermediate bonding layer and first envelope membrane layer facilitate coating of the parasite with the polymeric membrane. Subsequently, the negatively charged envelope membrane may then be sequentially coated with a positively charged polymer and, if desired, subsequent alternating layers of negatively and positively charged polymers to obtain the desired envelope membrane thickness.

For example, when using polyamino acid polymers containing charged carboxylate groups, for example, such as polyaspartic acid or polyglutamic acid, over a positively charged intermediate bonding layer, a coating of polyaspartic acid or polyglutamic acid can be applied followed by successive coating layers of polylysine, polyaspartic acid, etc.

Biocompatible semipermeable polymeric membranes which may be used to form the envelope membranes of the implant capsule include a wide variety of both biocompatible biodegradable polymers and biocompatible non-biodegradable polymers. A summary of suitable biodegradable polymers for use in preparing the present implant capsule can be found in R. Burns, "New Systems and Technologies in Drug Delivery", Conference Proceedings, Institute for International Research (1988). Specific examples of biodegradable polymers include poly(lactide-co-glycolide) (PLGA) polymers (R.K. Kulkarni, et al, Arch. Surg., (1966), 93:839–843); poly(epsilon-caprolactone) and copolymers thereof (C.G. Pitt and Z. Gu, J. Controlled Release, (1987), 4:283), poly(hydroxybutyric acid) and poly(hydroxyvalerate) copolymers; and poly(Cbz-Tyrosine-Tyrosine-Hexyl ester)iminocarbonate (J. Kohn, et al, J. Immunol. Methods, (1986), 95:31).

The permeability of the polymeric envelope membrane is a function of the molecular weight of the individual polymers and the thickness of the overall envelope coating layers. The molecular weight of the envelope polymers is generally in the range of about 5,000–300,000 daltons. The thickness of the envelope membrane coating will generally range between about 0.1–10 microns, preferably about 0.1–3 microns.

The implant capsules may be implanted by conventional intramuscular (IM), intraperitoneal (IP), subcutaneous or any other method of implantation conventionally used with diffusion chambers and the implantation of microencapsulated mammalian cells.

The present method and implant capsule are effective in treating disease associated with infection by parasites.

The present method is directed toward parasite infections caused by organisms of the phyla Protozoa, Platyhelminthes (flatworms) and Nemathelminthes (roundworms). Accordingly, the antigen-producing parasite which is encapsulated in the implant capsule are classified in these same phylae. Preferred parasites are taken from the groups Giardia, Toxocara, Leishmania, Trypanosoma, Entamoeba, Plasmodium, Toxoplasma, Schistosoma, Taenia, Dipylidium, Hymenolepis, Echinococcus, Ascaris, Ancyclostomatidae, Strongylida, Trichuris, Filaroidea]families and Onchocerca.

Specific examples of protozoan diseases to which the method is directed include giardiasis, toxoplasmosis, leishmaniasis, African trypanosomiasis, American trypanosomiasis and amebiasis as well as malaria. Typical flatworm infections include infections from organisms of the classes Trematoda (flukes) and Cestoda (tapeworms) and include schistosomiasis and cestodiases. Roundworm infections which may be treated by the present method include ascariasis, hookworm infections, stronglyoidiasis, trichuriasis, filarial disease and onchocerciasis, although the present method is not limited to these specific examples. A more complete list of parasitic diseases, which may be immunized against and are considered to be within the scope of the present method, may be found in Review of Medical Microbiology, 13th Ed., Lange Medical Publications, 1978, Chapter 41, pp. 512-514.

The antigen-producing parasite can be prepared according to known methods for collecting, washing and isolating infective parasite antigenic materials. Table 1 illustrates specific parasites and provides references for the preparation of these antigenic materials. Other parasites within the Phyla Protozoa, Platyhelminthes and Nemathelminthes not specifically identified in Table 1 are considered to be within the scope of the present invention and may be collected, isolated and prepared by processes similar to those disclosed in Table 1.

TABLE 1

| Parasite | Preparation of Antigen-Producing Parasites |
|---|---|
| | Reference |
| Strongylus vulgaris | (a) V. A. Dennis et al, Vet. Immunol. Immunopathol. (Netherlands), (1988), 20:61-74. |
| | (b) T. R. Klei et al, Vet. Parasitol. (Netherlands), (1983), 12:187-198. |
| Dirofilaria immitis | (a) Abraham et al, J. Parasit., (1988), 74:275. |
| Toxocara canis | (a) D. D. Bowman et al, Am. J. Trop. Hyg., (1987), 36:75-82. |
| Fasciola hepatica | (a) M. V. K. Sukhdeo et al, Int. J. Parasitol. (United Kingdom), (1988), 18:369-512. |
| | (b) H. Wedrychowicz et al, Acta Parasitol. Pol. (Poland), (1987), 32:369-382. |
| Leishmania species | (a) O. J. Pung et al, Int. J. Parasitol. (United Kingdom), (1988), 18:1053-1059. |
| | (b) J. I. Githure et al, Trans. R. Soc. Trop. Med. Hyg. (United Kingdom), (1988), 82:563. |
| | (c) R. H. Gorczynski, Infect. Immun. (USA), (1988), 56:1376-1381. |
| Toxoplasma gondii | (a) D. M. Israelski et al, Antimicrob. Agents Chemother. (USA), (1989), 33:30-34. |
| | (b) R. A. Payne et al, Epidemial. Infect. (United Kingdom), (1988), 100:205-212. |
| | (c) F. Santoro et al, C. R. Acad. Sci. (France), (1987), 304:297-300. |
| | (d) Y. Suzuki et al, Infect. Immun. (USA), (1987), 55:1017-1018. |
| | (e) U.S. Pat. No. 4,473,549 |

Microencapsulation of the parasites can be performed using encapsulation techniques which have previously been applied only to non-parasitic tissue, cells and bacteria. Encapsulation of parasites presents problems not encountered in the encapsulation of tissue, cells and bacteria. Specifically, parasites are capable of greater mobility which causes difficulties in the encapsulation process. The parasites must be made quiescent to become properly encapsulated. Problems associated with rapidly moving parasites are not present when one encapsulates tissue, cells or bacteria.

Additionally, living parasites require space within the implant capsule which enables the organism to move without tearing the capsule membranes. Adequate space is provided by first covering the parasite with the intermediate bonding layer and subsequently encapsulating with the envelope polymers. If the larva is not completely covered with the intermediate bonding layer/envelope polymers, or if inadequate space is provided within the capsule, tearing of the envelope polymers is possible which may lead to infection of the host organism. Implant capsules containing parasites can be efficiently prepared by the use of appropriate intermediate bonding layer materials and envelope polymers.

Preferred microencapsulation processes are those involving the formation of parasite/intermediate bonding layer drops or droplets such as described by Lim and Sun, Science, (1980), 210:908-910 and in U.S. Pat. Nos. 4,251,387; 4,352,883; 4,931,909; 4,409,331; 4,407,957 and 4,696,286. These references are incorporated herein by reference to provide a more complete description of microencapsulation processes which may be used to prepare the implant capsules of the present invention.

Another preferred microencapsulation process which may be used to encapsulate the parasites is the process of Rha et al (U.S. Pat. Nos. 4,749,620 and 4,744,933) in which capsules are formed by adding drops of a solution of either a cationic or anionic polymer to a solution of the ionic polymer of opposite charge. In this method, the parasite is first coated with the intermediate bonding layer and then sprayed or added dropwise as a particle to a solution of the negatively charged polymer. For example, a parasite coated with an intermediate bonding layer comprising agar or agarose and aluminum hydroxide may be sprayed into or added dropwise to a solution of polyaspartic acid or polyglutamic acid. The envelope membrane forms at the interface between the coated parasite and the anionic polymer. The specifications of U.S. Pat. Nos. 4,749,620 and 4,744,933 are incorporated herein by reference to provide a more complete description of this embodiment.

In another preferred embodiment, water-in-oil emulsions may be used to encapsulate the parasites coated with an intermediate bonding material. This process can be performed according to Nielson et al, Nature, 302 (1983).

The microencapsulation method of the present invention utilizes an intermediate bonding layer and a polymeric capsule envelope layer. The intermediate bonding layer creates a "template" for the polymer microcapsule envelope membrane and a second layer constituting the capsule membrane(s) itself. U.S. Pat. No. 4,251,387 discloses a preferred two-phase process for encapsulation of aqueous droplets by polymerization at the phase boundaries. In another preferred embodiment of the present method, parasites are suspended in a growth medium and injected through a nozzle capable of forming droplets (Lim and Sun, loc. cit.). The droplets are then dropped into a solution of polylysine and calcium. The calcium gels the alginate or agar and the polylysine produces a membrane. Removal of the calcium ions causes the alginate or agar to ungel leaving the parasites suspended in a polylysine capsule. Applicants have found that by using these processes and an appropriate intermediate bonding layer, parasites can be successfully encapsulated, remain viable and produce antigens for extended periods of time.

An alternative preferred encapsulation method is described in U.S. Pat. Nos. 4,696,286 for the production of tissue transplants, specifically pancreatic tissue. An intermediate "template" bonding layer is prepared by coating the transplant tissue with a polyfunctional material which acts as a bonding bridge between the transplant material and the outer polymeric envelope layer. Applicants have discovered that the process of U.S. Pat. No. 4,696,286 may also be used to encapsulate parasites and thereby prepare the implant capsules of the present invention.

Particularly preferred encapsulation processes involve coating the parasites with an intermediate bonding layer containing of aluminum hydroxide, in particular a mixture of $Al(OH)_3$ and agar or agarose. Aluminum hydroxide having a particle size of approximately 1-3 microns and agar are prepared as a solution in physiological saline. The aluminum hydroxide/agar solution is then mixed with a growth medium in which parasites have been suspended. After several minutes, clusters (droplets) of parasites containing one or more parasites are sedimented out. The aluminum hydroxide/agar coated clusters may then be encapsulated in a membrane of a polyanionic polyamino acid polymer, such as polyaspartic acid, or polyglutamic acid by mixing the aluminum hydroxide/agar coated clusters with a solution of the polyanionic polyamino acid according to one of the methods described above. After washing to remove residual polyanionic polymer, the polyanionic polymer coated clusters can be resuspended in a polycationic polyamino acid polymer, such as poly-L-lysine, whereby a polycationic membrane is formed over the polyanionic membrane. The negatively charged polyanionic polymer membrane and the positively charged polycationic membranes are attracted and result in a stable immunoisolated parasite cluster which is viable and provides slow release of parasite antigens. If desired, the polyanionic polymer and polycationic polymer forming steps and subsequent washes may be repeated one or more times to provide a thicker membrane envelope.

In another preferred variation, the aluminum hydroxide/agar may be replaced by a coating of a polycationic polyamino acid followed by coatings of polyaspartic acid and polylysine as noted above. A particularly preferred polycationic polyamino acid is poly-L-lysine, which may be used both for the initial coating layer and subsequent polylysine membrane layers. Repeated polyaspartic acid and polylysine membrane coatings are also possible with this embodiment.

The method of the present invention allows one to adjust the semipermeable nature of the coating membrane to control the diffusion of low molecular weight compounds out of the implant capsule. By varying the number of repetitions of the coating process, for example coatings of polyaspartic acid and polylysine, as well as by varying the molecular weight of the polyanionic and polycationic polymers themselves, one can control the molecular weight upper limit of diffusible antigens. Additional control of the antigenicity of the implant capsules can be obtained by varying the amount of aluminum hydroxide or agar in the initial template coating of the parasites and by the inclusion of known antigenic polymers to the initial coating of aluminum hydroxide/agar or polylysine. Known antigenic polymers include polytyrosine, polyhydroxybutyric acid, etc. These methods allow one to produce implant capsules with a specific "diffusion window" and allow control of antigenic materials diffusing out of the implant capsule. The specific number of coatings and/or thickness of the coating membrane layers can readily be determined by one skilled in the art utilizing known methods for measuring antigen secretion from encapsulated antigenic materials.

The implant capsules produced by the present process may contain a single antigen-producing parasite or may contain a multiplicity of parasites. The implant capsules generally range in size from about 50 to 500 microns and are therefore substantially smaller than diffusion chambers. Preferred microcapsules have an average capsule size which is about 1.5-3.0 times the size of the encapsulated larvae.

Antigen production by the implant capsules can be monitored in vitro and in vivo by known methods for analyzing excretory-secretory antigens produced by parasites. These methods include ELISA methods for antigen detection. The ELISA assay may be coupled with gradient pore polyacrylamide gel electrophoresis (PAGE) and analyzed to provide a profile of the antigens produced by specific parasite larva. See, for example, J.E. Badley et al, J. Parasit., (1987), 73:593-600 which describes the analysis of Toxocara canis larval excretory-secretory antigens, their characterization and antibody recognition. See also D.D. Bowman et al, Am. J. Trop. Med. Hyg., (1987), 36:75-82. Malarial antigens have been studied by M.F. Good et al, Science, (1988), 242:574-577.

An additional method available to evaluate the ability of the encapsulated parasite to produce a slow release of antigens, to monitor this release, and the final criterion for determining effective immunization of an animal is to challenge the immunized animal, i.e., the animal containing the implant capsule, with infectious material and to observe the degree of protection. See D.D. Bowman, loc. cit., which describes a mouse model and challenge with infective Toxocara canis organisms.

By analyzing the amount of antigen produced by the parasites and the amount of antigen which diffuses through the semipermeable polymeric envelope of the implant capsule, one can tailor the construction of the implant capsule to provide a continuous slow release of parasite antigen.

The implant capsule of the present invention may be implanted at any position in the body of the animal which stimulates a protective response by the host animals immune system. Preferred sites of implantation will be determined by the desired rate of antigen release from the implant capsule as well as factors relating to destruction of the implant capsule by the host immune system, intervening membrane barriers, etc.

The present implant capsules may be produced using parasites which are actively producing antigen or, alternatively, may be produced by encapsulating life forms of the parasite which, while not producing antigen at the time of encapsulation, are capable of development within the implant capsule to a stage where antigens are produced. By encapsulating parasites at various stages in development, it is possible to provide a sustained slow release of parasite antigen for extended periods of time. Parasites in any stage of development may be encapsulated according to the present invention so long as the parasite is capable of producing antigen at some stage in its life cycle within the implant capsule. The preferred form for encapsulation is the infective larval form, since this form induces natural protective immunity.

Parasites which molt during later life stages may be encapsulated according to the present invention. The ability to encapsulate molting organisms such as filarial worms allows one to provide a longer continuous supply of parasite antigen. Additionally, the molting parasite may provide a broader spectrum of antigens as the parasite matures, thereby providing a broader spectrum of immunity.

The encapsulated larva may be stored by any method which enables the storage of unencapsulated larva. For example, the encapsulated larva may be placed in an appropriate culture medium for the particular parasite and stored or shipped in the tissue culture medium. Where appropriate, the encapsulated larvae may be frozen or lyophilized, such as, for example, when the parasite is encapsulated during an egg or cyst stage of development. Frozen or lyophilized organisms may be thawed, placed in culture medium and incubated to facilitate growth of antigen-producing parasitic stages of the organism.

The degree of immunization is determined by challenging the immunized animal with infective larvae. The observation of antibody production or decreased parasite numbers in the immunized animal provides a determination of established immunity. A single immunization or periodic immunization, for example annual immunization, may be required to maintain immunity depending on the specific parasite.

Other features of the invention will become apparent in the course of the following descriptions of exemplary embodiments which are given for illustration of the invention and are not intended to be limiting thereof. As used herein, the present tense indicates examples which have not been performed that are used to exemplify the present invention, and past tense indicates examples which have been already performed.

EXAMPLES

Example 1

Adult *Toxocara canis* are collected from the feces of dogs after deworming with pyrantel pamoate. The female worms are dissected and the anterior one-third of the uterus is placed in a 1 wt.% sodium hydrochloride solution. The hydrochloride solution is then stirred for 10 minutes, filtered and centrifuged for three minutes at 2,000 x g. The supernatent is discarded and the egg-containing pellet is washed twice with distilled water and once with 0.5 wt.% formalin. Eggs isolated in this manner may be resuspended in 0.5 wt.% formalin and stored at room temperature. After approximately four weeks, the eggs are examined to ensure that they are infective and then washed with water to remove the formalin prior to encapsulation.

Aluminum hydroxide is ground to a particle size of about 1-3 microns and prepared as a 1 wt.% solution with physiological saline. Infective larvae prepared as in the method described above are then suspended in the aluminum hydroxide solution and mixed for several minutes. The aluminum hydroxide coated larvae are sedimented out and the excess aluminum hydroxide solution is removed. The aluminum hydroxide coated larvae are then washed three times with physiological saline.

Alternatively, the infective larvae prepared as described above are suspended in a solution of aluminum hydroxide and agar. The aluminum hydroxide/agar solution is prepared as a 0.5 wt.% aluminum hydroxide solution and a 1 wt.% agar or agarose solution with physiological saline. The infective larvae are suspended in the aluminum hydroxide/agar solution and mixed for several minutes followed by sedimentation and removal of excess aluminum hydroxide/agar solution as described above.

The aluminum hydroxide or aluminum hydroxide/agar coated larvae are transferred to a solution of poly-L-aspartic acid (0.5 wt.% in physiological saline, pH 7, Mw =50,000) and mixed for four minutes. The poly-L-aspartic acid is removed and the coated larvae are washed three times with saline.

The poly-L-aspartic acid coated larvae are then resuspended in poly-L-lysine (0.5 wt.% in physiological saline, Mw =50,000) and mixed for five minutes. The poly-L-lysine solution is then removed and the poly-L-lysine coated larvae are washed three times with physiological saline to produce an implant capsule. If desired, the poly-L-aspartic acid and polylysine coatings and the associated washes may be repeated to provide a thicker membrane coating.

Example 2

Infective *Toxocara canis* larva are prepared in a manner analogous to Example 1.

The infective larvae are suspended in a polylysine solution (0.5 wt.% in physiological saline, pH 7, Mw =50,000) for ten minutes with stirring. The polylysine coated larvae are sedimented out and the excess polylysine solution is removed. The polylysine coated larvae are then washed three times with physiological saline.

The polylysine coated larvae may then be encapsulated in poly-L-aspartic acid and poly-L-lysine, respectively in a manner analogous to Example 1 to produce an implant capsule.

Example 3

BALB/c BYJ, male, 7-week-old mice (Jackson Laboratories, Bar Harbour, Maine) are each mildly anesthesized with Metofane ® (Pitman-Moore, Inc., Washington Crossing, New Jersey) and 100 microliters of blood is withdrawn from the retroorbital plexus of each mouse with a capillary pipet. Each mouse is given approximately 500 implant capsules prepared according to Examples 1 or 2 in 0.5 suitable buffer administered subcutaneous. The mice are bled from the retroorbital plexus on the day of infection, weekly for the first six weeks post-infection and every other week for the following 2 months. The blood collected each week is pooled and the sera are stored at −70° C. ELISA analysis and antibody recognition tests show production of antigens for *Toxocara canis*.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An implant capsule for immunizing an animal against parasite infection, comprising at least one antigen-producing parasite coated with a positively charged intermediate bonding material and encapsulated within one or more semipermeable polymeric envelope membranes, wherein said parasite is a mammalian parasite within the Phyla Protozoa, Platyhelminthes or Nemathelminthes.

2. An implant capsule for immunizing an animal against parasite infection, comprising at least one antigen-producing parasite coated with a positively charged intermediate bonding material and encapsulated within one or more semipermeable polymeric envelope membranes, wherein said parasite is an organism selected from the group consisting of parasites from the groups Toxocara, Giardia, Leishmania, Trypanosoma, Entamoeba, Toxoplasma, Plasmodium, Schistosoma, Taenia, Dipylidium, Hymenolepis, Echinococcus, Ascaris, Ancyclostomatidae, Strongylida, Trichuris, Filaroidea and Onchocerca.

3. An implant capsule for immunizing an animal against parasite infection, comprising at least one antigen-producing parasite coated with a positively charged intermediate bonding material and encapsulated within one or more semipermeable polymeric envelope membranes, wherein said parasite is selected from the group consisting of Toxocara canis, Strongylus vulgaris, Dirofilaria immitis, Fasciola hepatica, Leishmania braziliensis, Leishmania donovani, Leishmania mexicana, Trypanosoma cruzi and Toxoplasma gondii.

4. The implant capsule of claim 1, wherein said polymeric envelope membrane is a polycationic polyamino acid polymer, a polyanionic polyamino acid polymer, or a combination thereof.

5. An implant capsule for immunizing an animal against parasite infection, comprising at least one antigen-producing parasite coated with a positively charged intermediate bonding material and encapsulated within one or more intermediate bonding material and encapsulated within one or more semipermeable polymeric envelope membranes, wherein said polymeric envelope membrane is a polycationic polyamino acid polymer, a polyanionic polyamino acid polymer, or a combination thereof and said polycationic polyamino acid is polyarginine, polylysine, or polyornithine.

6. The implant capsule of claim 4, wherein said polyanionic polyamino acid is polyaspartic acid, or polyglutamic acid.

7. An implant capsule for immunizing an animal against parasite infection, comprising at least one antigen-producing parasite coated with a positively charged intermediate bonding material and encapsulated within one or more semipermeable polymeric envelope membranes, wherein said polymeric envelope membrane is a polycationic polyamino acid polymer, a polyanionic polyamino acid polymer, or a combination thereof and said intermediate bonding material comprises a polysaccharide-containing material and a biocompatible gellable metal hydroxide.

8. The implant capsule of claim 7, wherein said intermediate bonding layer comprises a mixture of aluminum hydroxide with agar, agarose, alginate, or chitosan or mixtures thereof.

9. The implant capsule of claim 1, wherein said intermediate bonding layer is a polycationic polyamino acid.

10. The implant capsule of claim 9, wherein said polycationic polyamino acid is polylysine.

11. An implant capsule for immunizing an animal against parasite infection, comprising at least one antigen-producing parasite coated with a positively charged intermediate bonding material and encapsulated within one or more semipermeable polymeric envelope membranes, wherein said intermediate bonding material contains an immunologic adjuvant.

12. The implant capsule of claim 11, wherein said adjuvant is an antigenic polymer, a lymphokine or a cytokine.

13. An implant capsule for immunizing an animal against parasite infection, comprising at least one antigen-producing parasite coated with a positively charged intermediate bonding material and encapsulated within one or more semipermeable polymeric envelope membranes, wherein said polymeric envelope membrane is a biocompatible biodegradable polymer selected from the group consisting of poly(lactide-co-glycolide) polymers, poly(epsiloncaprolactone) polymers and copolymers thereof, poly(hydroxybutyric acid)-poly(hydroxyvalerate) copolymers and poly(Cbz-tyrosine-tyrosinehexyl ester) iminocarbonate.

14. An implant capsule for immunizing an animal against parasitic infection, wherein said implant capsule is prepared by the steps of:
(a) suspending a parasite capable of producing antigens in an aqueous growth medium;
(b) coating said parasite with a gellable positively charged intermediate bonding material; and
(c) encapsulating said coated parasite with a polyanionic semipermeable polymeric envelope, membrane.

15. The implant capsule of claim 14, wherein said coating step is conducted by contacting said suspended parasite with a solution of aluminum hydroxide, a polycationic polyamino acid, agar, agarose, alginate, chitosan or mixtures thereof to form a coated parasite droplet.

16. The implant capsule of claim 15, wherein said coated parasite droplet is further contacted with a solution of a polyanionic polyamino acid polymer and then with a solution of a polycationic polyamino acid polymer.

17. The implant capsule of claim 16, wherein said polyanionic polyamino acid is polyaspartic acid, or polyglutamic acid and said polycationic polyamino acid is polylysine, polyarginine or polyornithine.

18. The implant capsule of claim 15, wherein said parasite is suspended in a mixture of aluminum hydroxide with at least one of agar, agarose, alginate or chitosan, and said droplets are contacted with a solution of polylysine and calcium ions, whereby said alginate is gelled and said polylysine forms said semipermeable polymeric envelope membrane.

19. The implant capsule of claim 15, wherein said parasite is suspended in the mixture of aluminum hydroxide with at least one of agar, agarose, alginate or chitosan, and said droplets are contacted with a solution of a polyanionic amino acid to encapsulate said coated parasite.

20. A method of immunizing an animal against parasitic infection, comprising the step of implanting into an animal, an implant capsule comprising at least one antigen-producing parasite coated with a positively charged intermediate bonding material and encapsulated within one or more semipermeable polymeric envelope membranes; at a location in said animal sufficient to stimulate a protective immune response in said animal to said parasite antigen.

21. The method of claim 20, wherein said parasite is a mammalian parasite within the Phyla Protozoa, Platyhelminthes or Nemathelminthes.

22. The method of claim 21, wherein said parasite is an organism selected from the group consisting of parasites from the groups Toxocara, Giardia, Leishmania, Trypanosoma, Entamoeba, Plasmodium, Schistosoma, Taenia, Dipylidium, Hymenolepis, Echinococcus, Ascaris, Ancyclostomatidae, Strongylida, Trichuris, Filaroidea and Onchocerca.

23. The method of claim 20, wherein said polymeric envelope membrane is a polycationic polyamino acid polymer, a polyanionic polyamino acid polymer, or a combination thereof.

24. The method of claim 23, wherein said polycationic polyamino acid is polylysine.

25. The method of claim 23, said polyanionic polyamino acid is polyaspartic acid.

26. The method of claim 20, wherein said intermediate bonding material comprises a mixture of aluminum hydroxide with agar, agarose, alginate, chitosan or mixtures thereof.

27. The method of claim 20, wherein said intermediate bonding layer is aluminum hydroxide.

28. The method of claim 20, wherein said intermediate bonding layer is a polycationic polyamino acid.

29. The method of claim 28, wherein said polycationic polyamino acid is polylysine.

30. The method of claim 19, wherein said polymeric envelope membrane is a biocompatible biodegradable polymer selected from the group consisting of poly(lactide-co-glycolide) polymers, poly(epsilon-caprolactone) polymers and copolymers thereof, poly(hydroxybutyric acid-)poly(hydroxyvalerate) copolymers and poly(Cbz-tyrosine-tyrosine-hexyl ester) iminocarbonate.

31. The method of claim 20, wherein said intermediate bonding material contains an immunologic adjuvant.

32. The method of claim 31, wherein said immunologic adjuvant is an antigenic polymer, a lymphokine or a cytokine.

* * * * *